(12) United States Patent
Kreidemacher et al.

(10) Patent No.: US 12,427,248 B2
(45) Date of Patent: Sep. 30, 2025

(54) OVERMOLDED SEPTUM

(71) Applicant: Roche Diabetes Care, Inc., Indianapolis, IN (US)

(72) Inventors: Oliver Kreidemacher, Lorsch (DE); Olaf Lebau, Hofheim am Taunus (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 952 days.

(21) Appl. No.: 17/350,853

(22) Filed: Jun. 17, 2021

(65) Prior Publication Data

US 2021/0308373 A1 Oct. 7, 2021

Related U.S. Application Data

(63) Continuation of application No. PCT/EP2019/085472, filed on Dec. 17, 2019.

(30) Foreign Application Priority Data

Dec. 19, 2018 (EP) .................... 18213982

(51) Int. Cl.
| | |
|---|---|
| *A61M 5/162* | (2006.01) |
| *A61J 1/14* | (2023.01) |
| *A61M 5/142* | (2006.01) |
| *A61M 39/02* | (2006.01) |
| *A61M 39/04* | (2006.01) |

(Continued)

(52) U.S. Cl.
CPC ............ *A61M 5/162* (2013.01); *A61M 5/142* (2013.01); *A61M 39/0247* (2013.01); *A61M 39/04* (2013.01); *B29C 45/1711* (2013.01); *B29C 45/561* (2013.01); *A61M 2039/0072* (2013.01);

(Continued)

(58) Field of Classification Search
CPC .. A61M 5/162; A61M 5/142; A61M 39/0247; A61M 39/04; A61M 2039/0072; A61M 2039/027; A61M 2205/0216; A61M 2039/0054; A61M 2039/0081; A61M 39/00; A61M 5/158; A61M 39/045; A61M 39/06; A61M 39/10; A61M 2039/062;

(Continued)

(56) References Cited

U.S. PATENT DOCUMENTS

| | | | |
|---|---|---|---|
| 5,804,499 | A | 9/1998 | Dehm et al. |
| 2002/0029022 | A1 | 3/2002 | Naritomi et al. |

(Continued)

FOREIGN PATENT DOCUMENTS

| | | |
|---|---|---|
| EP | 2 528 642 A2 | 12/2012 |
| JP | H 02-147131 U | 12/1990 |

(Continued)

OTHER PUBLICATIONS

International Search Report and Written Opinion of the International Searching Authority, PCT/EP2019/085472, Feb. 20, 2020, 8 pages.

*Primary Examiner* — Jason E Flick

(74) *Attorney, Agent, or Firm* — Bose McKinney & Evans LLP

(57) ABSTRACT

Disclosed is a pierceable septum for use in drug reservoirs and infusion sets. The pierceable septum has an elastic core made from a core material and a surround made from a surrounding material. The surrounding material is more rigid than the core material. The elastic core is fully embedded in the surround.

12 Claims, 4 Drawing Sheets

(51) Int. Cl.
*B29C 45/17* (2006.01)
*B29C 45/56* (2006.01)
*A61M 39/00* (2006.01)

(52) U.S. Cl.
CPC ............... *A61M 2039/027* (2013.01); *A61M 2205/0216* (2013.01)

(58) Field of Classification Search
CPC .... A61M 2039/066; A61M 2039/1072; B29C 45/1711; B29C 45/561; A61J 1/1406
See application file for complete search history.

(56) References Cited

U.S. PATENT DOCUMENTS

| | | |
|---|---|---|
| 2006/0264898 A1 | 11/2006 | Beasley et al. |
| 2007/0066941 A1 | 3/2007 | Tezuka et al. |
| 2012/0296290 A1 | 11/2012 | Argauer et al. |
| 2013/0299021 A1 | 11/2013 | Gobbi Frattini |

FOREIGN PATENT DOCUMENTS

| | | | | |
|---|---|---|---|---|
| JP | H 10-55981 A | 2/1998 | | |
| JP | H 11-19177 A | 1/1999 | | |
| JP | 2000-140068 A | 5/2000 | | |
| JP | 2008-539025 A | 11/2008 | | |
| KR | 2006-0010822 A | 2/2006 | | |
| WO | WO 02/07804 A1 | 1/2002 | | |
| WO | WO 2004/103453 A1 | 7/2006 | | |
| WO | WO-2006116438 A2 * | 11/2006 | ......... | A61B 5/15003 |
| WO | WO-2012101101 A1 * | 8/2012 | ............ | A61J 1/1406 |

* cited by examiner

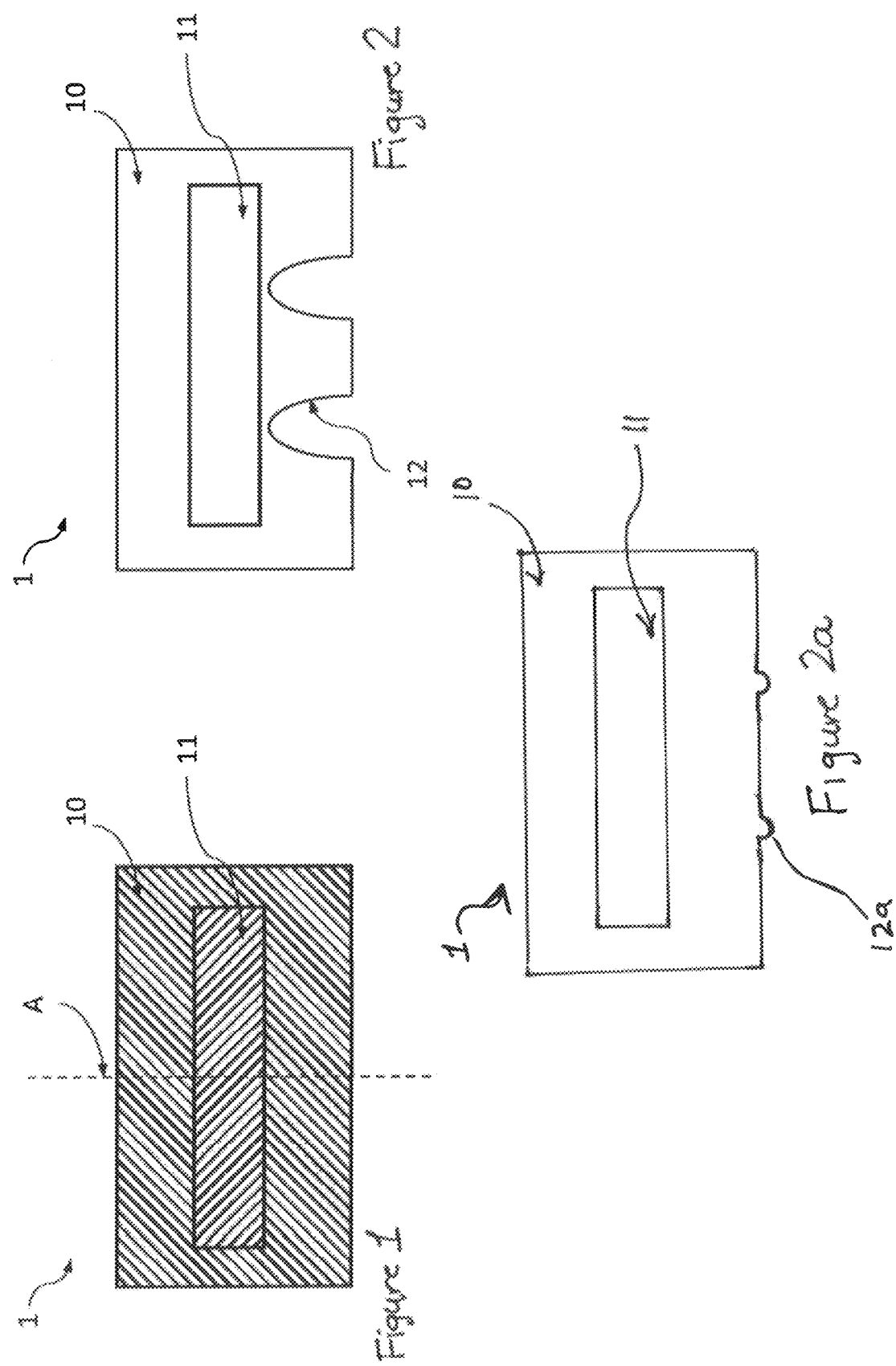

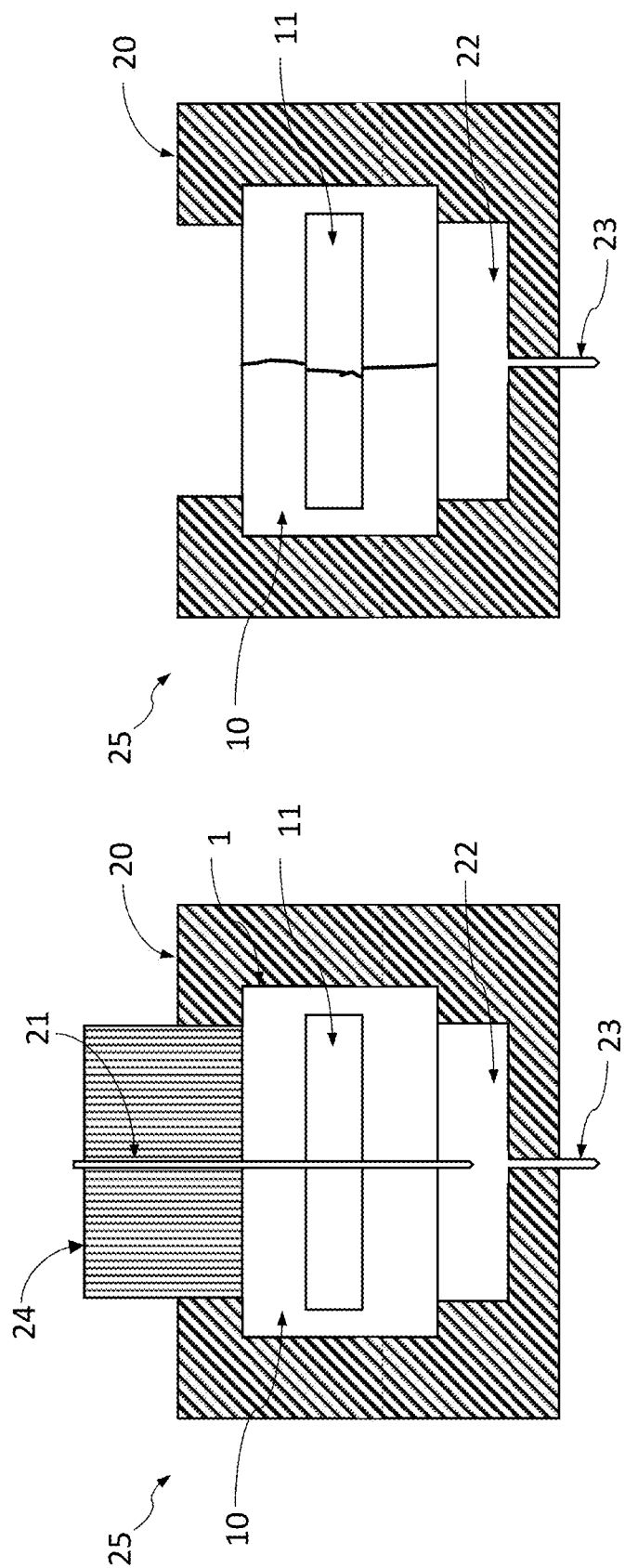

OVERMOLDED SEPTUM

RELATED APPLICATIONS

This application is a continuation of PCT/EP2019/085472, filed Dec. 17, 2019, which claims priority to EP 18 213 982.4, filed Dec. 19, 2018, the entire disclosures of both of which are hereby incorporated herein by reference.

BACKGROUND

This disclosure lies in the field of infusion or injection technology. More particularly, it is related to pierceable septa as used in infusion sets or reservoirs for liquid drugs, to infusion sets and reservoirs comprising a septum, as well as a method for producing a pierceable septum.

Ambulatory infusion sets are well known in the art. For example, in the therapy of Diabetes Mellitus they are used in combination with a miniaturized infusion pump for Continuous Subcutaneous Insulin Infusion (CSII) where small drug amounts are infused in a metered way via a cannula into the tissue of a patient. Such infusion sets can also be used in a number of further therapies, such as pain therapy or cancer therapy. They are available from a number of suppliers, such as Roche Diabetes Care GmbH, Germany, or Medtronic MiniMed Inc., CA, USA. For example in CSII, the metered doses in the range of microliters or nanoliters.

Although typical infusion sets and infusion systems are usually operated in a continuous manner and thus constantly carried by the patient, there are several daily routines, such as showering, swimming, etc. in which the pump and the tubing should be removed. In such events, it is in the interest of the patient and favorable for cost reasons that the cannula unit remains on the patient so that the flexible infusion cannula used to introduce drug into the patient's tissue is not removed. Therefore, infusion systems have been developed, comprising cannula units which can be easily disconnected from the remaining parts, in particular a tubing, by disconnection of a connector device. The connector device comprises a connector cannula, which is fluidly connected to a tubing and an infusion pump. However, upon each reconnection, the septum of the cannula unit is pierced by the connector cannula. As a result, the septum suffers multiple cuts, i.e., punctures, by the commonly employed sharp cannulas and therefore becomes more prone to leakage.

A wide variety of infusion sets for introducing a liquid drug into a patient's body rely on elastic septa, which may be pierced multiple times by a cannula or a needle. A typical infusion set can for example comprise a cannula unit, which can be fluidly connected to an infusion pump and/or a drug reservoir via a tubing with a connector device that has a connector cannula. Typically the cannula unit further comprises a compartment for a liquid drug, which is at least partially formed by a surface of a septum. In particular, the septum may be used for sealing this compartment which is essentially in permanent fluid connection to the patient's tissue via an infusion cannula. In such systems, liquid drug can be transferred to the compartment and subsequently to the patient via the connector cannula and the infusion cannula.

Furthermore, in regard to infusion sets, it is advantageous to employ flexible infusion cannulas for establishing a permanent fluid connection to the patient's tissue. Such flexible infusion cannulas, are inserted into the patient's tissue with the help of a piercing needle, such as a rigid steel needle, a section of which is initially arranged within a lumen of the infusion cannula, while a head section is arranged above the septum and the piercing needle penetrates the septum. After insertion of both the piercing needle and the flexible infusion cannula into the tissue, the piercing needle is retracted, while the flexible infusion cannula remains in the tissue. Either a single septum is used for both drug delivery and the introduction of the piercing needle, or alternatively, two different septa may be employed. Typical examples are described in WO 02/07804 A1, U.S. Publication No. 2012/296290 A1 and EP 2528642 A2.

In order to avoid leakage of the liquid drug and to avoid contamination from the outside, such septa are commonly cylindrically shaped and prestressed by radial compression. In such systems, the septum is built into a cannula housing, which compresses the septum. A further beneficial effect of the radial compression is that after penetration and subsequent removal of the needle or the cannula, the thus generated channel-shaped cut within the septum is compressed and the occurrence of leakage is favorably avoided or at least diminished.

As indicated above, one possible approach to achieve this goal is to prestress the septum by radial compression. However due to constructional constraints, the compression cannot be infinitively increased. Importantly, while radial compression of the septum indeed diminishes leakage of liquid drug in cases in which the septum has been pierced only once, leakage becomes problematic upon repeated piercing events. Furthermore, typical infusion systems employ infusion pumps, which deliver the liquid drug to the patient and therefore a fluidic pressure is exerted. As a result of the fluidic pressure, leakage becomes a severe problem, especially if the septum has been pierced already multiple times.

Furthermore, multi-layered septa are known in the art. These septa are produced by separate manufacturing of at least two layers, which may be made from different materials and which are subsequently connected to form a laminate. Afterwards, the typically cylindrical septa are obtained by punching the laminate.

Due to the above mentioned production process, multi-layered septa are very restricted in terms of their design. Typically, it is not possible to equip these septa with functional geometric shapes, such as a sealing lip, as their method of production inevitably provides thin, disk-shaped septa. Furthermore, the lamination step induces internal tension into the material, which leads to the occurrence of leakages upon penetration of the septum with a cannula. The final punching of the laminate initially compresses the septum, before the septum is punched out of the laminate. As a result, when the septum is finally punched out, its sides are rather uneven and not perfectly symmetric. When such a septum is employed for example in an infusion set, leakage between the septum and the housing often occurs. Thus, multi-layered septa may be suited for decreasing the occurrence of leakages between the cannula and the septum, however, these often lead to leakages between the septum and the housing of an infusion set.

In particular, multiple piercing with a cannula still represents a significant source for leakages. This is highly problematic, as firstly, in case of the small dosing units in the nanoliter range typically employed in continuous insulin infusion, any occurring undetected leakage may have a dramatic influence on dosage and thus on the patient's health. Secondly, many automated infusion devices comprise occlusion detection devices which are malfunctioning if operated in an untight system.

SUMMARY

This disclosure improves the state of the art regarding the design and use of elastic septa in the context of infusion and/or injection of liquid drugs, thereby avoiding disadvantages of the prior art fully or partly. The septum may in particular belong to an infusion set as used, for example, in CSII, or a drug reservoir.

In favorable embodiments, the improved septum provides a tight sealing by the septum even if pierced multiple times and/or if exposed to higher pressures.

Further in favorable embodiments, the septum can be manufactured in a cost-efficient way.

According to a first aspect of this disclosure, a pierceable septum for use in drug reservoir and infusion sets is taught. The septum comprises an elastic core from a core material and a surrounding (also referred to herein as a "surround") from a surrounding material. Additionally, the elastic core is fully embedded in the surround and the surrounding material is more rigid than the core material.

As the elastic core is fully embedded in the surround, the core is completely covered by the surround and is thus not exposed at the surface of the septum. This provides the advantage that the expansion behavior of the core material is significantly restricted. In contrast to a septum in which the elastic core is not fully embedded in the surround, the expansion of the elastic core upon penetration of the septum by a cannula is restricted from all sides of the elastic core. As the surrounding material is more rigid than the core material, a force acts on the core material, which is radially directed towards the penetrating cannula. As a result, any gaps between the cannula and the septum are avoided and the interface between cannula and septum is tightly sealed.

As used herein, the term "septum" is readily understood by those skilled in the art and is typically an engineered element, for example in the form of a membrane or plug, for sealingly separating a first side and second side in a fluid, i.e., gas and/or liquid tight seal, which can be pierced by a needle or a cannula. Typically, a septum does not comprise an opening or a puncture, which passes through the septum from the first side to the second side, before a needle or a cannula has been pierced through the septum. Consequently, a stump needle cannot be easily pierced through the septum without exerting high forces.

The septum may typically be made from elastomeric and/or thermoplastic-elastomeric materials, such as silicon or natural-rubber and rubber derivatives, i.e., isoprene rubber, butyl rubber, FKM, styrene-butadiene rubber, etc.

A pierceable septum according to this disclosure for use in drug reservoirs and infusion sets is essentially cylindrical or cuboid. Preferably, the septum has an essentially flat, plate-like shape. In this context, the term "essentially" is understood as to also include septa comprising for example one or more sealing lips and/or a circumferential groove.

The elastic core may have a cuboid shape. However, the core may also be spherical or have any other suitable shape. Typically, the elastic core is flat and elongated in the lateral direction of the septum. The lateral direction of the septum is normal to the puncturing path of a cannula.

A pierceable septum according to this disclosure may typically have a diameter or width of 2 to 20 mm, preferably 2 to 6 mm, more preferably 3 to 4 mm.

Typically, the thickness of the septum, i.e., the distance a cannula needs to pierce in an operative state, may be 1 to 10 mm, preferably 1 to 5 mm, more preferably 1 to 2 mm.

Furthermore, the skilled person understands how to determine whether a first material is more rigid than a second material. For example, this may be achieved by measuring and comparing the shore hardness of the materials. Typically, a shore durometer is commonly used in the art for this purpose. The higher the shore hardness of a material, the greater is the resistance to indentation and thus the harder the material. Thus, a more rigid material is also a harder material. This difference in rigidity of the core and surrounding material offers the advantage that upon retraction of the cannula an offset may be generated in the channel-shaped cut, which results from the puncture of the needle. Due to this offset, the sealing of the septum is significantly increased and leakage avoided.

In typical embodiments, the elastic modulus of the core material is smaller than the elastic modulus of the surrounding material.

Preferably, the shear modulus is used herein as the elastic modulus. In an embodiment according to this disclosure, the elastic restoring force of the core is smaller than the elastic restoring force of the surround. As it is known to the person skilled in the art, the elastic restoring force is directly influenced by the hardness and/or the elastic modulus of the layer. In such embodiments, upon retraction of the cannula an offset may be generated in the channel-shaped cut, which results from the puncture of the needle.

Typically, the pierceable septum is integrally designed, that is the elastic core and the surround are fixedly connected to each other.

In preferred embodiments, the surrounding material has a shore hardness, which is chosen such that the expansion of the core material upon penetration of the septum with a cannula is confined.

In other embodiments, the surrounding material has a shore hardness of 0 to 100 Shore A, preferably 50 to 80 Shore A, and/or the core material has a shore hardness of 0 to 50 Shore A, preferably 10 to 40 Shore A. Such a hardness is particularly advantageous, as the outer material is rigid enough for providing efficient confinement of the expansion of the core material, which is concomitantly tightly sealed upon removal of the cannula.

In preferred embodiments, the elastic core of the pierceable septum is overmolded by the surround. This has the advantage that the elastic core and the surround are fixedly connected without the use of any additional adhesives.

In further embodiments, the core material is an elastomer and/or the surrounding material is an elastomer and/or a thermoplastic elastomer. For example in certain embodiments, a mixture of an elastomer and a thermoplastic elastomer may be used. A particular example includes a mixture of silicone and a thermoplastic elastomer.

In further embodiments, the elastic core is radially prestressed by the surround. The term "radial compression" as used herein refers to a force which is exerted towards the piercing path of a cannula, i.e., an axis intersecting the center of a first surface and the center of an opposing second surface of the septum. In these embodiments, the surround is constructed in a way that it prestresses the core by radial compression. Thus, the sealing of the interface between a penetrating needle and the septum is even further improved. These embodiments improve the state of the art regarding the design of elastic septa in the context of infusion and/or injection of liquid drugs, as the occurrence of leakage is efficiently avoided or at least significantly reduced.

In preferred embodiments, the septum additionally comprises at least one sealing lip, shown as sealing lip 12a in FIG. 2a, which also serves to avoid leakage. Alternatively or additionally, the septum may comprise a circumferential groove. If a higher pressure is applied to a first surface comprising the circumferential groove as compared to an opposing second surface of such an embodiment in an operated state, (i) an axis-directed component of a force, which is exerted on the first surface acts towards an axis which intersects the center of the first surface and the center of the second surface, and (ii) an edge-directed component of the force which is exerted on the first surface acts opposite to an axis which intersects the center of the first surface and the center of the second surface.

Thus, a circumferential groove further reduced the occurrences of leakages at the interface between a puncturing cannula and the septum, at the remaining through cut after removal of the cannula and at the interface between a cannula housing and the septum.

In other embodiments, the surround may comprise two or more different materials. For example, the material along the piercing path of the cannula may be less rigid than the material aside from the piercing path. Thus, in such an embodiment, the fully embedded elastic core may be surrounded by at least two different materials. In these embodiments, the elastic core material is the least rigid material and the surrounding material aside from the piercing path of the cannula is the most rigid material, while the rigidity of the surrounding material within the piercing path lies in between. The piercing path may be indicated by optical or haptic means. According to another aspect of this disclosure, a method for producing a pierceable septum is provided. The method comprises the steps of providing an elastic core from a core material and fully overmolding the elastic core with a surrounding material to produce a pierceable septum with an elastic core, wherein the elastic core if fully embedded in a surround.

In a preferred embodiment, the overmolding is performed by injection molding, preferably by 2 k molding.

According to a further aspect of this disclosure, an infusion set comprising a pierceable septum is taught.

Typically, the septum in an infusion set is radially prestressed by radial compression.

According to a further aspect of this disclosure, the overall objective is achieved by a reservoir for liquid drugs comprising a pierceable septum according to this disclosure.

Typically, the septum in a drug reservoir is radially prestressed by radial compression.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1 shows a cross-sectional view of a pierceable septum in accordance with one embodiment of this disclosure;

FIGS. 2 and 2a show cross-sectional views of a pierceable septum in accordance with other embodiments of this disclosure.

FIG. 5(a) shows a cross-sectional view of a pierceable septum built into a housing in accordance with another embodiment of this disclosure;

FIG. 5(b) shows a cross-sectional view of a pierceable septum built into a housing in accordance with another embodiment of this disclosure.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

An advantageous embodiment of a pierceable septum 1 according to this disclosure is shown in FIG. 1. The pierceable septum 1 comprises an elastic core 11, from a core material and a surround 10 from a surrounding material. As can be readily seen, the elastic core is fully embedded in the surround. In other words, the elastic core is completely arranged inside the surround. Thus, the elastic core is neither visible nor extends to the surface of the septum nor can be in contact with any other parts, such as a housing or a drug reservoir. The elastic core in the embodiment shown is essentially flat and elongated in the lateral direction of the septum. FIG. 1 also illustrates axis A, which extends along the piercing path of a cannula and which is essentially normal to the lateral direction of the septum.

FIG. 2 illustrates another embodiment of this disclosure. In addition to elastic core 11 and surround 10, the pierceable septum 1 further comprises circumferential groove 12 (for clarity reasons, no filling of the core and the surrounding is used as in FIG. 1). Typically, if such a septum is used in an infusion set or drug reservoir, the surface of the septum comprising groove 12 is facing the inside of the infusion set or drug reservoir and the opposing flat surface is positioned on the outside of the infusion set or reservoir.

Figure 3:
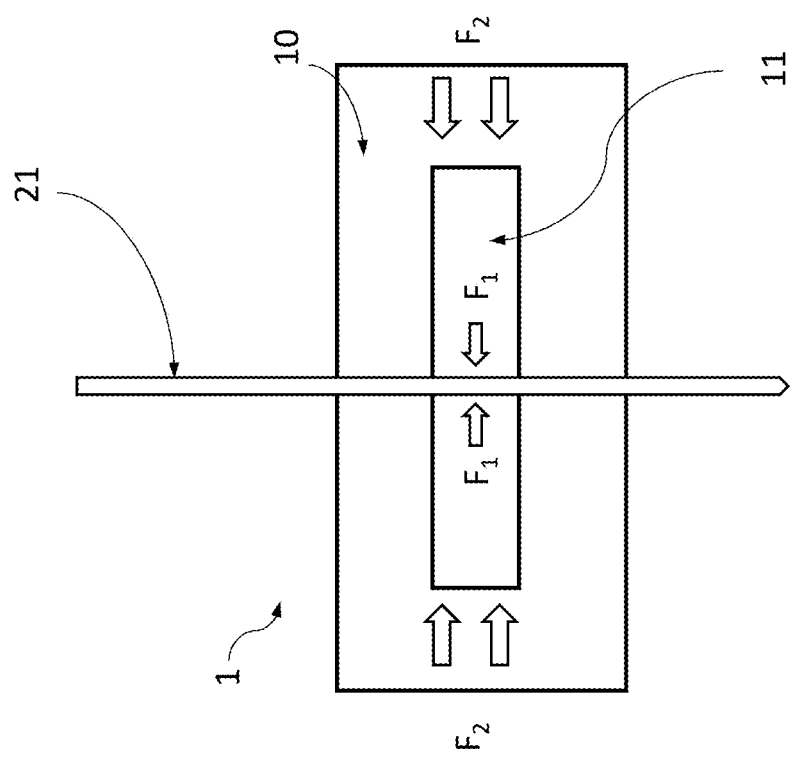
FIG. 3 shows a cross-sectional view of a pierceable septum in accordance with another embodiment of this disclosure.

FIG. 3 shows a septum 1 according to this disclosure, which is penetrated by cannula 21 along a piercing path. As indicated by the arrows, the surround 10 exerts a force $F_2$ on elastic core 10, upon which the elastic core sealingly engages the cannula ($F_1$). Thus, a septum according to this disclosure may significantly increase the friction between a cannula and the septum.

Figure 4:
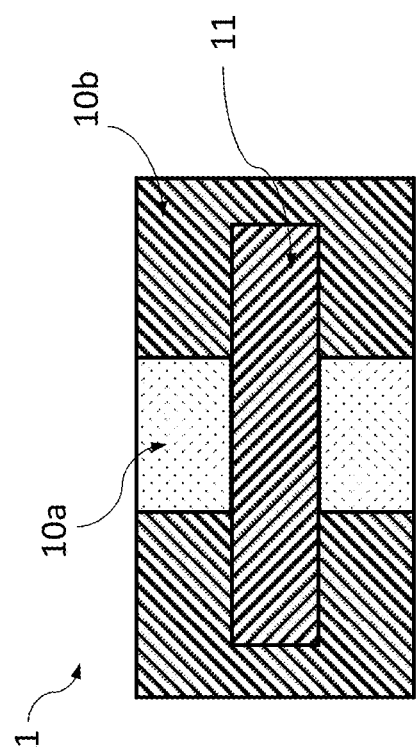
FIG. 4 shows a cross-sectional view of a pierceable septum in accordance with another embodiment of this disclosure.

FIG. 4 illustrates a further advantageous embodiment of a pierceable septum 1 according to this disclosure. The surround 10 comprises two different materials. The material along the piercing path of a cannula (see 10a), may be less rigid than the material aside from the piercing path (see 10b). As a result, elastic core 11 is surrounded by two different materials. Such an embodiment has the beneficial effect that it enables smooth piercing of the septum along a predetermined piercing path and still provide the above described sealing effect by laterally engaging a penetrating cannula.

FIG. 5(a) depicts a pierceable septum 1 according to this disclosure, which is built into a housing unit 20. The housing unit 20 is part of a cannula unit 25, which itself can be part of an infusion set. Additionally, cannula unit 25 may comprise a flexible infusion cannula 23 which can be inserted into the patient's tissue by insertion of a piercing needle through the septum, prior to assembly of removable connector device 24. As can be readily seen, the housing unit 20 and the septum form a compartment 22, which can comprise a liquid drug. For example, the drug can be pumped under pressure into compartment 22 by an infusion pump (not shown), which is in fluid connection with connector cannula 21. Connector cannula 21 is part of connector device 24, which is removably connected to cannula unit 25 and not depicted in greater detail. The state shown in FIG. 5(*a*) represents the operative state of the infusion set, in which the infusion pump is in fluid connection with flexible infusion cannula 21 via compartment 22 and connector cannula 21.

FIG. 5(*b*) shows the cannula unit 25 of FIG. 5(*a*), in which the user may have disconnected the infusion pump from the connector device 24 by withdrawal of connector cannula 21 from septum 1. Such a process may for example be performed by the user in situations, in which an infusion pump may be unsuitable, for example while taking a shower. As indicated by the curved lines, withdrawal of the connector cannula 21 leaves a puncture or through cut in the septum. Due to the fact that the surrounding material is more rigid than the core material, respectively due to the difference in elastic modulus of elastic core 11 and surround 10, an offset of the through cut is generated, that is, the through cut is not continuous, but the trough cut in the core 11 is laterally displaced as compared to the through cut in the surround 10. This offset significantly decreases the occurrence of any leakage, which becomes even more relevant in the event of multiple piercings.

Figure 6:
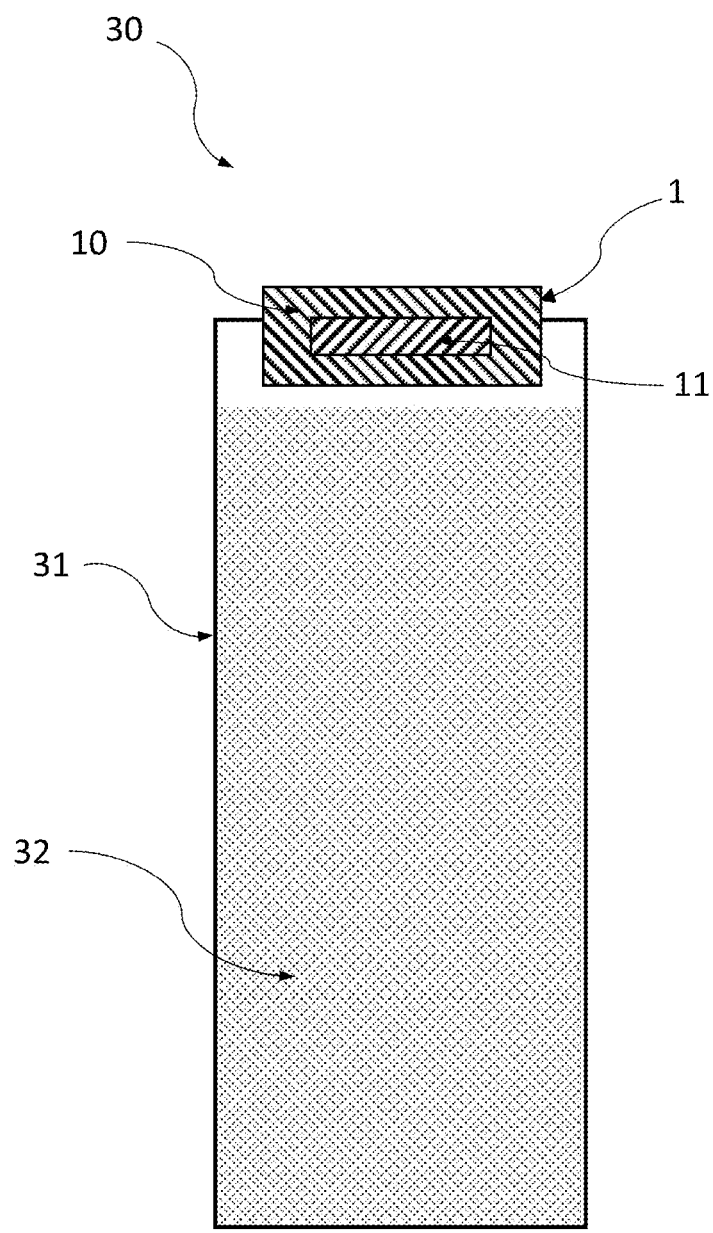
FIG. 6 shows a cross-sectional view of a pierceable septum built into reservoir for drugs in accordance to another embodiment of this disclosure.

FIG. 6 shows a reservoir for drugs 20, for example an insulin cartridge comprising walls 31 and liquid drug 32. A pierceable septum 1 according to this disclosure allows for withdrawal of drug 32 from the reservoir by a cannula and ensures tight sealing of the pierced septum 1 during penetration of the cannula and also after its removal. The particular septum 1 shown comprises core 11 which is fully embedded in surround 10.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A pierceable septum for use in drug reservoirs and infusion sets, the pierceable septum comprising:
   an elastic core formed from a core material; and
   a surround formed from a surrounding material;
   wherein, the elastic core is fully embedded in the surround and the surrounding material is more rigid than the core material;
   further wherein the surround comprises first and second different surrounding materials, wherein the first surrounding material is disposed along a piercing path of a cannula and the second surrounding material is disposed aside from the piercing path, further wherein the first surrounding material is less rigid than the second surrounding material.

2. The pierceable septum according to claim 1, wherein the surrounding material has a shore hardness selected from the group consisting of: from 0 to 100 Shore A and from 50 to 80 Shore A.

3. The pierceable septum according to claim 1, wherein the core material has a shore hardness selected from the group consisting of from 0 to 50 Shore A and from 10 to 40 Shore A.

4. The pierceable septum according to claim 1, wherein the elastic core is overmolded by the surround.

5. The pierceable septum according to claim 1, wherein the core material is an elastomer.

6. The pierceable septum of claim 1, wherein the surrounding material is an elastomer or thermoplastic elastomer.

7. The pierceable septum according to claim 1, wherein the elastic core is radially pre-stressed by the surround.

8. The pierceable septum according to claim 1, wherein the septum comprises a sealing lip or a circumferential groove.

9. An infusion set comprising a pierceable septum according to claim 1.

10. The infusion set according to claim 9, wherein the septum is radially prestressed by radial compression.

11. A reservoir for a liquid drug comprising a pierceable septum according to claim 1.

12. The reservoir according to claim 11, wherein the septum is radially prestressed by radial compression.

* * * * *